(12) United States Patent
Justmann et al.

(10) Patent No.: US 8,012,911 B2
(45) Date of Patent: Sep. 6, 2011

(54) METHODS TO INCREASE CROP YIELD

(75) Inventors: Thomas Justmann, Waupaca, WI (US);
Michael Weber, Sunnyvale, CA (US);
Ray Hoobler, Pleasanton, CA (US);
David Cope, Los Gatos, CA (US);
Timothy Knight, Raleigh, NC (US)

(73) Assignee: Purfresh, Inc., Fremont, CA (US)

( * ) Notice: Subject to any disclaimer, the term of this patent is extended or adjusted under 35 U.S.C. 154(b) by 0 days.

(21) Appl. No.: 12/490,271

(22) Filed: Jun. 23, 2009

(65) Prior Publication Data
US 2010/0024072 A1    Jan. 28, 2010

Related U.S. Application Data

(60) Provisional application No. 61/132,908, filed on Jun. 23, 2008.

(51) Int. Cl.
*A01N 25/00* (2006.01)
(52) U.S. Cl. ..................... 504/116.1; 504/103
(58) Field of Classification Search ............... 504/116.1, 504/103; 800/298; 424/717; 700/231
See application file for complete search history.

(56) References Cited

U.S. PATENT DOCUMENTS

| 6,069,112 A * | 5/2000 | Glenn et al. | 504/119 |
| 2005/0261133 A1 * | 11/2005 | Nakanishi et al. | 504/358 |
| 2009/0186768 A1 * | 7/2009 | Hoobler et al. | 504/362 |
| 2009/0192038 A1 * | 7/2009 | Hoobler et al. | 504/116.1 |

OTHER PUBLICATIONS

DeMarsay et al. Guidelines for Developing an Effective Fungicide Spray Program for Wine Grapes in Maryland 2007, pp. 1-9.*
Gamagae et al. Evaluation of post-harvest application of sodium bicarbonate-incorporated wax formulation and *Candida oleophila* for the control of anthracnose of papaya. Crop Protection 23 (2004) 575-579.*
Ramsdel. Common Diseases of the Grapevine in Michigan. MSUE Bulletin E-1732 Oct. 1994, last modified May 23, 2003, pp. 1-8.*
OVATION 500 Selective Herbicide, Mar. 2002, pp. 1-6.*
PURSHADE Solar Crop Protectant, May 21, 2008, one page.*
SURROUND Crop Protectant for Plant Surface Protection 2005, 4 pp.*

* cited by examiner

*Primary Examiner* — June Hwu
(74) *Attorney, Agent, or Firm* — Carr & Ferrell LLP (57) ABSTRACT

Provided herein are exemplary methods for increasing crop yield. One exemplary method for increasing a yield of a crop includes controlling plant tissue stress by at least partially coating a plant tissue with a composition comprising an agricultural sunscreen formulation and a second agricultural chemical. The agricultural sunscreen formulation and the second agricultural chemical may be applied to the plant tissue from separate containers, wherein each container either contains the agricultural sunscreen formulation or the second agricultural chemical. Further, the agricultural sunscreen formulation and the second agricultural chemical may be applied to the crop at or near the same time. Alternatively, the agricultural sunscreen formulation and the second agricultural chemical may be applied to the crop from a shared container, wherein the shared container contains both the agricultural sunscreen formulation and the second agricultural chemical.

20 Claims, 5 Drawing Sheets

METHODS TO INCREASE CROP YIELD

CROSS-REFERENCE TO RELATED APPLICATION

This application claims the benefit and priority of U.S. Provisional Patent Application Ser. No. 61/132,908 filed on Jun. 23, 2008 titled "Method to Increase Yield for Row Crops," which is hereby incorporated by reference.

This application is related to U.S. Non-Provisional patent application Ser. No. 12/313,192 filed on Nov. 17, 2008 titled "Systems and Methods for Applying Particle Films to Control Stress on Plant Tissues," and this application is related to U.S. Non-Provisional patent application Ser. No. 12/291,875 filed on Nov. 14, 2008 titled "Sunscreen Formulations for Use in the Production of Organic Crops," both of which are hereby incorporated by reference.

BACKGROUND OF THE INVENTION

1. Field of the Invention

This invention relates to protecting plant tissues from stress, and more specifically to methods to increase crop yield.

2. Description of Related Art

Crops such as corn, soybean, canola, sunflowers, wheat, sugar beets and cotton are grown in large quantities and traditionally have small profit margins for the grower. Most of the cost of agricultural production is fixed per acre of land farmed, and the profit for the farmer depends on yield (i.e. the amount of product harvested per acre). A typical example is given in Table 1 (below):

| | | | |
|---|---|---|---|
| COSTS | Seed Corn | $50 | |
| | Fertilizer | $200 | |
| | Tillage | $100 | |
| | Pesticides | $50 | |
| | Harvest | $50 | |
| | Miscellaneous | $50 | |
| | Total: | $500 | per acre |
| INCOME | Yield | 140 | bushels |
| | Market Price | $5 | per bushel |
| | Total: | $700 | per acre |
| PROFIT | Total | $200 | per acre |

In the example shown in Table 1, a small increase in yield (e.g., from 140 to 147 bushels per acre, or 5%) translates into a significant increase in profits (e.g., 15%). Conversely, a decrease in yield (e.g., from 140 to 100 bushels per acre) can destroy the profits. It is therefore desirable for farmers to increase crop yield.

SUMMARY OF THE INVENTION

Provided herein are exemplary methods for increasing crop yield. One exemplary method for increasing crop yield includes controlling plant tissue stress by at least partially coating the plant tissue with a composition comprising an agricultural sunscreen formulation and a second agricultural chemical. The agricultural sunscreen formulation and the second agricultural chemical may be applied to the crop from separate containers, wherein each container either contains the agricultural sunscreen formulation or the second agricultural chemical. Further, the agricultural sunscreen formulation and the second agricultural chemical may be applied to the crop at or near the same time. Alternatively, the agricultural sunscreen formulation and the second agricultural chemical may be applied to the crop from a shared container, wherein the shared container contains both the agricultural sunscreen formulation and the second agricultural chemical.

Among other things, plant tissue stress may be caused at least in part by solar stress, a fungus, an insect, a weed and/or a bacterial or viral pathogen. According to some exemplary embodiments, the second agricultural chemical may be a pesticide, which may further comprise a herbicide, a fungicide, or an insecticide. The plant tissue may be at least partially coated with an effective amount of the agricultural sunscreen formulation and/or with an effective amount of the pesticide. Alternatively, the plant tissue may be at least partially coated with an effective amount of the composition of the agricultural sunscreen formulation and the second agricultural chemical, wherein the amount of the second agricultural chemical required in order to be effective is less than what would otherwise be required for an individual application of the second agricultural chemical (without the accompanying application of the agricultural sunscreen formulation). The agricultural sunscreen formulation may comprise on a weight to weight basis about 40% to 80% calcium carbonate, about 1% to 5% bicarbonate, sodium or potassium salt, and about 15% to 59% water. Further, the agricultural sunscreen formulation may have a viscosity from about 1,000 to about 45,000 centipoise.

Another exemplary embodiment may include a plant tissue substrate selected from a group consisting of field crops, fruits, vegetables, trees, flowers, grasses, roots, landscape and ornamental plants, wherein the plant tissue substrate is at least partially coated with a composition comprising an agricultural sunscreen formulation and a second agricultural chemical.

DETAILED DESCRIPTION OF THE INVENTION

Increased worldwide demand for commodity crops has triggered a dramatic increase in market prices. Ethanol production from corn is one of these drivers. As a result, farmers are growing crops in areas that are less than optimal for successful farming. For example, farmers are attempting to grow crops in climates that are much hotter than is preferred for a particular crop. Even in established agricultural regions, global climate change has resulted in hotter weather with increased solar radiation. In plants, heat stress resulting from solar radiation results in reduced transpiration and photosynthesis, and as a result, plants exposed to heat stress die or produce fewer seeds (i.e. yields decrease).

A critical phase in the production cycle of a crop is the time between plant seedling emergence and the time when the crop is mature enough to provide for its own protection by forming a canopy. Generally, this is a period of about 6-10 weeks after emergence. During this time, factors that "program" the yield are locked in. For example, young corn plants set cobs and are susceptible to a variety of factors that may create stress.

Pests of various kinds create stress. Pests include weeds, fungi (molds), insects, bacteria and viruses. The farmer will usually apply sprays of pesticides at certain critical times in the growth cycle to control stress and plant deterioration from pests. Pesticides include but are not limited to herbicides (to reduce or kill weeds), fungicides (to reduce or kill fungi) and insecticides (to reduce or kill insects). For the purpose of this specification, pesticide is defined as any substance that reduces or kills pests, including a direct action as well as indirect action (for example, making the plant less desirable for insects).

One of the most important stressors is weeds. Weeds, if not controlled, compete with the crop seedlings for sunlight and nutrients. Lack of weed control may lead to the death of young plants or reduced yield from those plants. Sophisticated methods have been developed to deal with this problem. One method involves a regime of herbicide applications, such as glyphosate-containing formulations, in combination with seed for plants that are tolerant to these herbicides. A single herbicide spray treatment may be sufficient to obtain the desired effect, as additional spray treatments are not desirable because of cost.

Another example of an important stressor is plant pathogens. If not controlled, they can significantly reduce marketable yield. Lack of control leads to significant reduction in total yield and a reduction in the quality of produce for market. Sophisticated methods have been developed to deal with this problem. One method involves a regime of fungicide applications, for example, pyraclostrobin containing formulations which help control or reduce the negative impact of the plant pathogens to the crop.

In addition, solar stress is increasingly becoming a concern. Solar stress may include detrimental effects of high ultraviolet ("UV") and infrared ("IR") radiation which can kill living cells or damage DNA, so the cell changes its function. Solar stress also is created by the increased plant temperature due to absorption of heat radiation (long-wave radiation) which heats parts of the plant to temperatures higher than the ambient air temperature, reducing yield at harvest. Solar stress may be mitigated by shading, but shading is not economically feasible for a large planted acreage. Accordingly, it would be desirable to have a means for protecting crops from solar stress while at the same time protecting crops from weeds, pests, and/or pathogens.

It has been found that applying a particle film that provides solar protection during critical phases of plant development has surprising benefits for increased crop yield.

During times of stress but also in general during phases of growth, plants benefit from micronutrients that are applied to the foliage.

Figure 1:
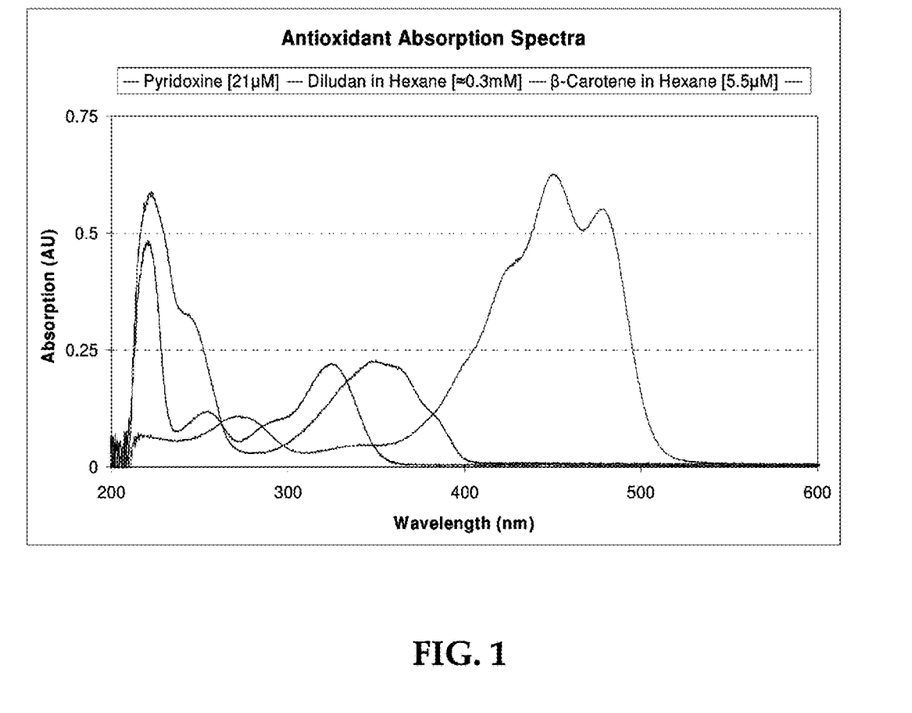
FIG. 1 shows an exemplary absorption spectra for pyridoxine, diludan in hexane and beta carotene in hexane.

For the farmer, it is very desirable to take measures to apply pesticidal treatments and nutrient treatments at the same time in order to save costs. For example, a typical cost for an aerial spray is $12/acre for a fungicide, and $12/acre for the aerial application. It makes sense to apply other substances, whether these are foliar micronutrients or particle films, at the same time.

The various exemplary methods provided herein increase crop yield. One exemplary method for increasing crop yield includes controlling plant tissue stress by at least partially coating the plant tissue with a composition comprising a particle film such as an agricultural sunscreen formulation and a second agricultural chemical. The agricultural sunscreen formulation and the second agricultural chemical may be applied to the crop from separate containers, wherein each container either contains the agricultural sunscreen formulation or the second agricultural chemical. Further, the agricultural sunscreen formulation and the second agricultural chemical may be applied to the crop at or near the same time. Alternatively, the agricultural sunscreen formulation and the second agricultural chemical may be applied to the crop from a shared container, wherein the shared container contains both the agricultural sunscreen formulation and the second agricultural chemical. Yield of glyphosate-resistant crops may also be increased by applying an agricultural sunscreen formulation to reduce solar stress in combination with a glyphosate-containing herbicide formulation. The application may either be a simultaneous tank mix of the agricultural sunscreen formulation and the glyphosate-containing herbicide, or a sequential application from separate containers. The former is preferred because of lower cost.

According to a further exemplary embodiment, a herbicide is used in combination with a sunscreen formulation to protect row crops from solar stress and to increase yield. Particle film sunscreens have proven to be particularly effective in protecting plant tissues such as leaves, seeds and fruit from solar radiation by blocking or scattering solar radiation, including damaging UV radiation.

For field spray application, two methods are possible. In the preferred embodiment, the sunscreen and the herbicide are either provided in a single formulation, or mixed together from separate components immediately prior to spraying plants in the field. In another embodiment, the pesticide is applied first, followed by subsequent application of the sunscreen formulation, or vice versa. The formulations are typically provided as a concentrate which is diluted with water upon filling a spray tank.

The formulations are preferably provided as a liquid concentrate or wettable granules to minimize weight, reduce transportation costs, and to provide easy handling. However, the ingredients may be mixed together or applied in many different ways. Independent of the method of application, according to various exemplary embodiments, the total amount of particles sprayed ranges from about 1 pound per acre to about 50 pounds per acre in order to be effective.

In the preferred embodiment, the formulation contains fine particles comprising on a weight to weight basis at least 10% w/w and preferably >50% w/w of a concentrate. The medium particle diameter is <10 μm and preferably <4 μm. Particles less than 4 μm in size are preferred because they are particularly effective at scattering and reflecting UV light. They are also easier to keep in an aqueous suspension for easy mixing and application; larger particles settle out quickly. In the preferred embodiment, the particle material is calcium carbonate but other materials may be used, such as kaolin, bentonite, carnuba wax or various combinations thereof. Also, silica and silicates may be used as a major, trace or inert ingredient.

FIG. 1 shows an exemplary absorption spectra for pyridoxine, diludan in hexane and beta carotene in hexane. These three materials represent exemplary selective light absorbing materials. The protective action of particles may be enhanced by the addition of a wavelength selective light absorbing material having a maximum absorbance in a specific wavelength range. The absorbing material is chosen so that its maximum absorbance is at wavelengths which are particularly effective for preventing degradation of the pesticide and/or preventing damage of the plant. It is desirable that the absorber is a material commonly and safely used in agricultural production. If separate sunscreen and pesticide formulations are used in a combinative way, the light absorber is preferably part of the sunscreen component but can also be part of the pesticide formulation.

Many substances and plant cells are affected by UV light, so the light absorber should be effective in the UV range, according to various exemplary embodiments. Many antioxidants may fulfill this requirement, for example, diludan or pyridoxine whose absorption spectra are shown in FIG. 1. Of these two, pyridoxine is preferred because it is water soluble and more cost-efficient. In contrast, another commonly used antioxidant, β-carotene is less desirable for applications for UV protection; even though it has some absorption in the UV range, most of its absorption is in the visible range. However, β-carotene would be preferred if the pesticide to be protected is sensitive to solar radiation in the photosynthetically active wavelength range of approximately 400-500 nm.

The formulations or compositions described herein may be further augmented by the addition of stress-mitigating compounds or nutrients.

Additionally, the stress in row crops may be reduced by spraying the seeded field with a reflective sunscreen formulation just prior to emergence, or right after emergence. The appearance of the ground will be its normal color plus white or milky-white areas. Observed from the air, a field treated in this manner may appear brighter and whiter than surrounding fields. The temperature of the ground, and of the air immediately above the ground, will be reduced due to reflection of solar radiation.

In the preferred embodiment, the application in combination with the pesticide occurs between the time of seedling emergence and the emergence of a canopy, or the first 6-10 weeks after emergence.

Figure 2:
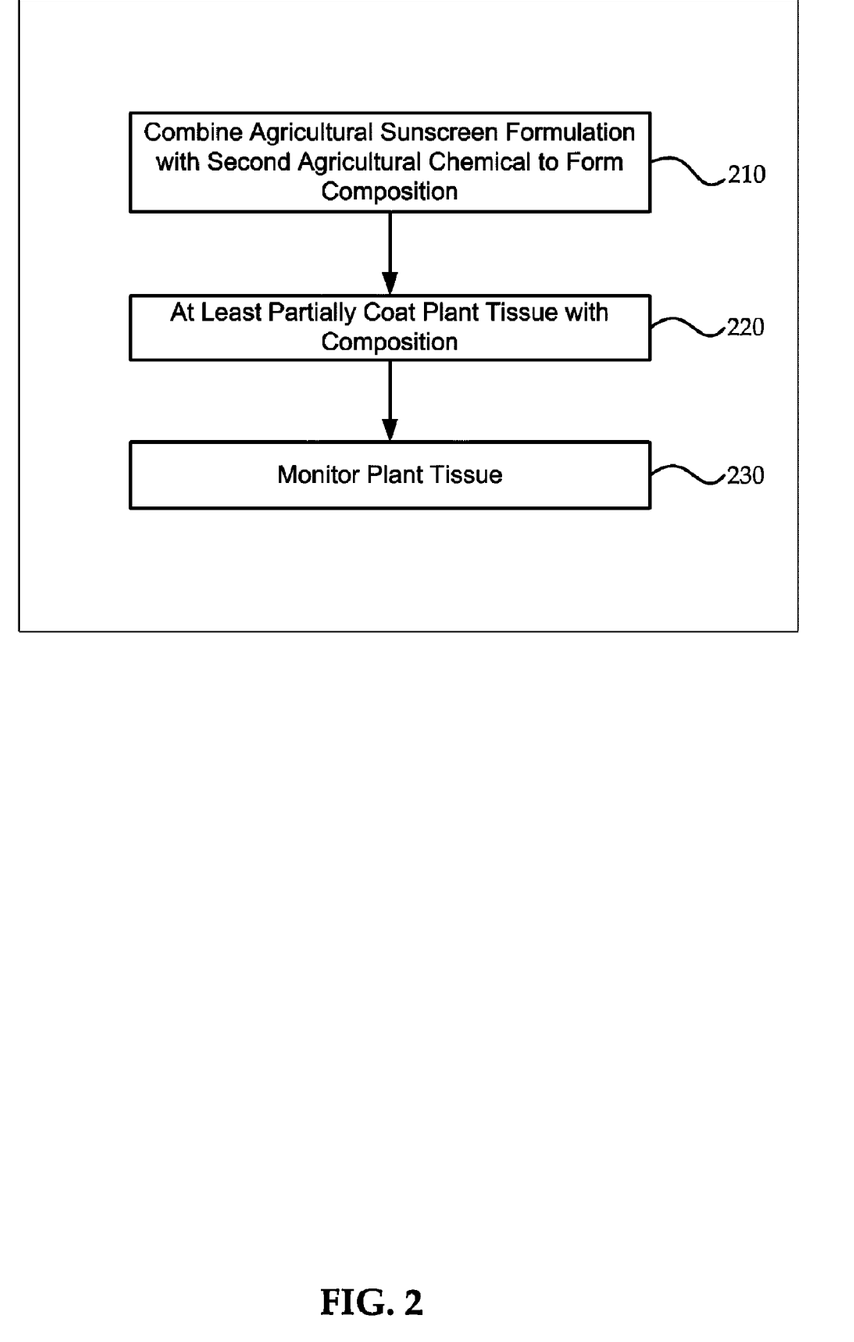
FIG. 2 is a flow chart of an exemplary method for increasing crop yield.

FIG. 2 is a flow chart of an exemplary method for increasing crop yield.

At step 210, an agricultural sunscreen formulation and a second agricultural chemical are combined to form a composition. An alternative exemplary method includes applying the agricultural sunscreen formulation and the second agricultural chemical from separate containers, wherein each container either contains the agricultural sunscreen formulation or the second agricultural chemical.

Below are examples of natural (i.e. permitted for organic use) and traditional agricultural sunscreen formulations. Formulas 6, 14 and 15 represent exemplary compositions of an agricultural sunscreen formulation and a second agricultural chemical (i.e. Chlorothalonil or Dicofol).

Wettable Powders ("WP"):
Formula 1:
80-90% calcium carbonate.
1.0-20% bicarbonate, sodium or potassium salt.
0-5% dispersant (sodium dioctyl sulfosuccinate).
Formula 2:
80-90% calcium carbonate.
2-20% linosulfonate salt, sodium or calcium.
0-5% dispersant.
Formula 3:
80-90% calcium carbonate.
2-20% chitin.
0-5% dispersant.
Formula 4:
80-90% calcium carbonate.
2-20% sulfur.
0-5% dispersant.
Formula 5:
80-90% calcium carbonate.
2-30% copper sulfate.
0-5% dispersant.
Formula 6:
50-90% calcium carbonate (sunscreen).
50-80% Chlorothalonil (fungicide).
0-5% dispersant (dioctyl sulfosuccinate).
Formula 7:
50-90% calcium carbonate.
2-30% copper soap (copper octanoate).
0-5% dispersant.
Water Dispersible Granule ("WDG"):
Formula 8:
50-90% calcium carbonate.
0.5-5% dispersant, sodium dioctyl sulfosuccinate.
0.5-10% water.
0-20% binder (clay, bentonite).
10-20% potassium or sodium salt of bicarbonate.
Formula 9:
50-90% calcium carbonate.
0.5-5% dispersant, sodium dioctyl sulfosuccinate.
0.5-10% water.
0-20% binder (clay, bentonite).
10-20% lignosulfonate salts of sodium or calcium.
Formula 10:
50-90% calcium carbonate.
0.5-5% dispersant, sodium dioctyl sulfosuccinate.
0.5-10% water.
0-20% binder (clay, bentonite).
2-20% Chitin.
Formula 11:
50-90% calcium carbonate.
0.5-5% dispersant, sodium dioctyl sulfosuccinate.
0.5-10% water.
0-20% binder (clay, bentonite).
2-30% Sulfur.
Formula 12:
50-90% calcium carbonate.
0.5-5% dispersant, sodium dioctyl sulfosuccinate.
0.5-10% water.
0-20% binder (clay, bentonite).
2-30% copper sulfate.
Formula 13:
50-90% calcium carbonate.
0.5-5% dispersant, sodium dioctyl sulfosuccinate.
0.5-10% water.
0-20% binder (clay, bentonite).
2-30% copper soap (copper octanoate).
Formula 14:
50-90% calcium carbonate (sunscreen).
50-80% Chlorothalonil (fungicide).
0.5-5% dispersant, sodium dioctyl sulfosuccinate.
0.5-10% water.
0-20% binder (clay, bentonite).
Formula 15:
50-90% calcium carbonate (sunscreen).
50-80% Dicofol (insecticide).
0.5-5% dispersant, sodium dioctyl sulfosuccinate.
0.5-10% water.
0-20% binder (clay, bentonite).

According to some exemplary embodiments, the second agricultural chemical may be a pesticide, which may further comprise a herbicide, a fungicide, or an insecticide.

At step 220, a plant tissue is at least partially coated with the composition formed at step 210.

In various exemplary embodiments, the agricultural sunscreen formulation and the second agricultural chemical may be applied to the plant tissue from separate containers, wherein each container either contains the agricultural sunscreen formulation or the second agricultural chemical. Further, the agricultural sunscreen formulation and the second agricultural chemical may be applied to the crop at or near the same time. Alternatively, the agricultural sunscreen formulation and the second agricultural chemical may be applied to the crop from a shared container, wherein the shared container contains both the agricultural sunscreen formulation and the second agricultural chemical. The plant tissue may be at least partially coated with an effective amount of the agricultural sunscreen formulation and/or with an effective amount of the pesticide. Alternatively, the plant tissue may be at least partially coated with an effective amount of the composition of the agricultural sunscreen formulation and the second agricultural chemical, wherein the amount of the second agricultural chemical required in order to be effective is less than what would otherwise be required for an individual application of the second agricultural chemical (without the accompanying application of the agricultural sunscreen formulation).

At step 230, the plant tissue is monitored. According to various exemplary embodiments, the monitoring of plant tissues may include the collection of data. The data may be obtained via one or more plant tissue sensors. The data may include soil moisture data, transpiration data, irrigation data and/or solar flux data. For example, sap-flow measurements based on the heat balance principle may provide a direct measurement of transpiration and may be monitored remotely. Other methods may provide similar data, including measurements of stomatal conductance, stem water potential, etc. Other types of data (especially data pertaining to water loss through plant tissues) may be obtained and fall within the scope of the various embodiments described herein.

In yet a further embodiment, the current plant tissue stress data may be obtained by weather sensors. Such data may include air temperature data, ground temperature data, humidity data, solar radiation data, and/or wind speed and direction data. Other types of data may be obtained and fall within the scope of the various embodiments described herein.

Figure 3:
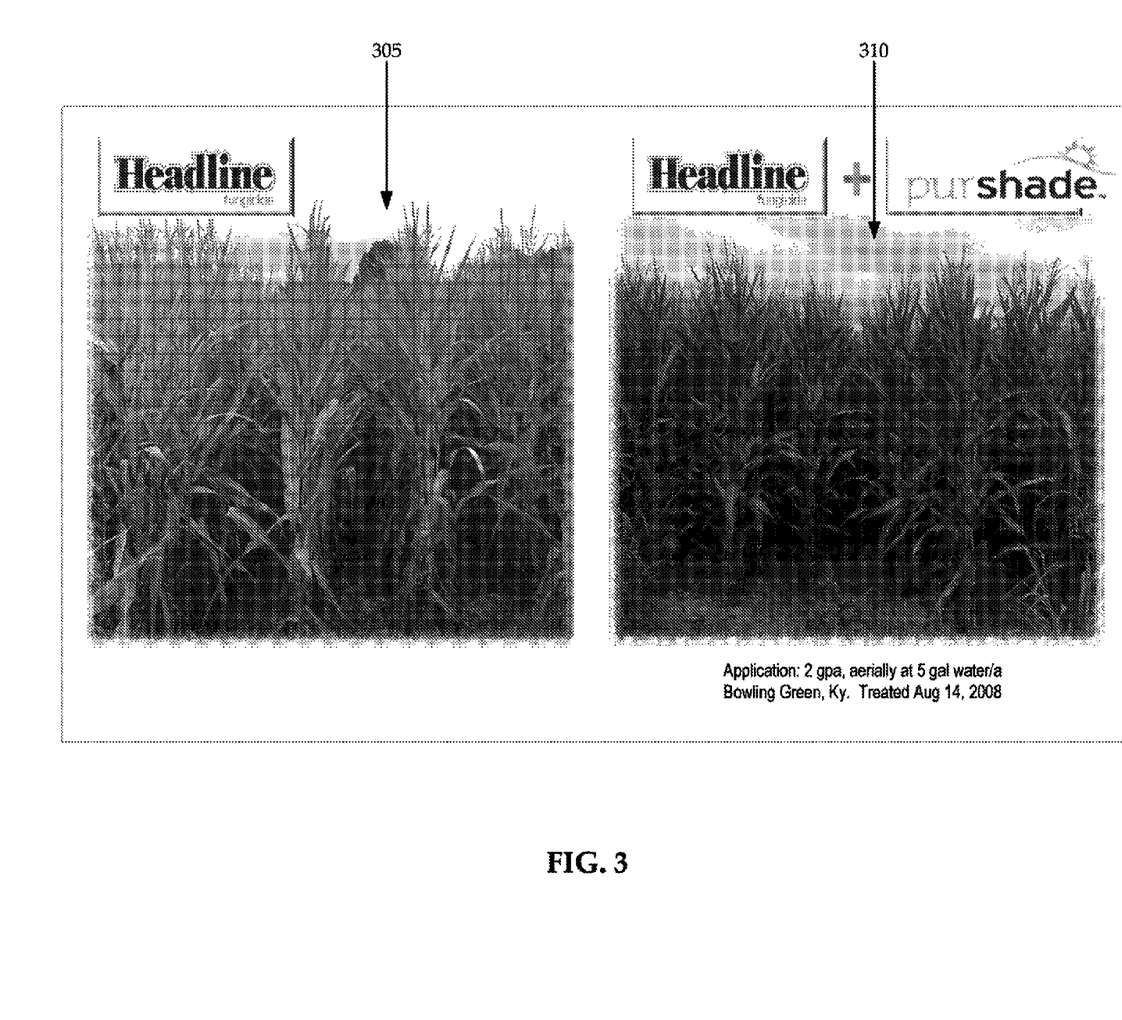
FIGS. 3-4 are photographs showing exemplary increased crop yield results in connection with Example One.
Figure 4:
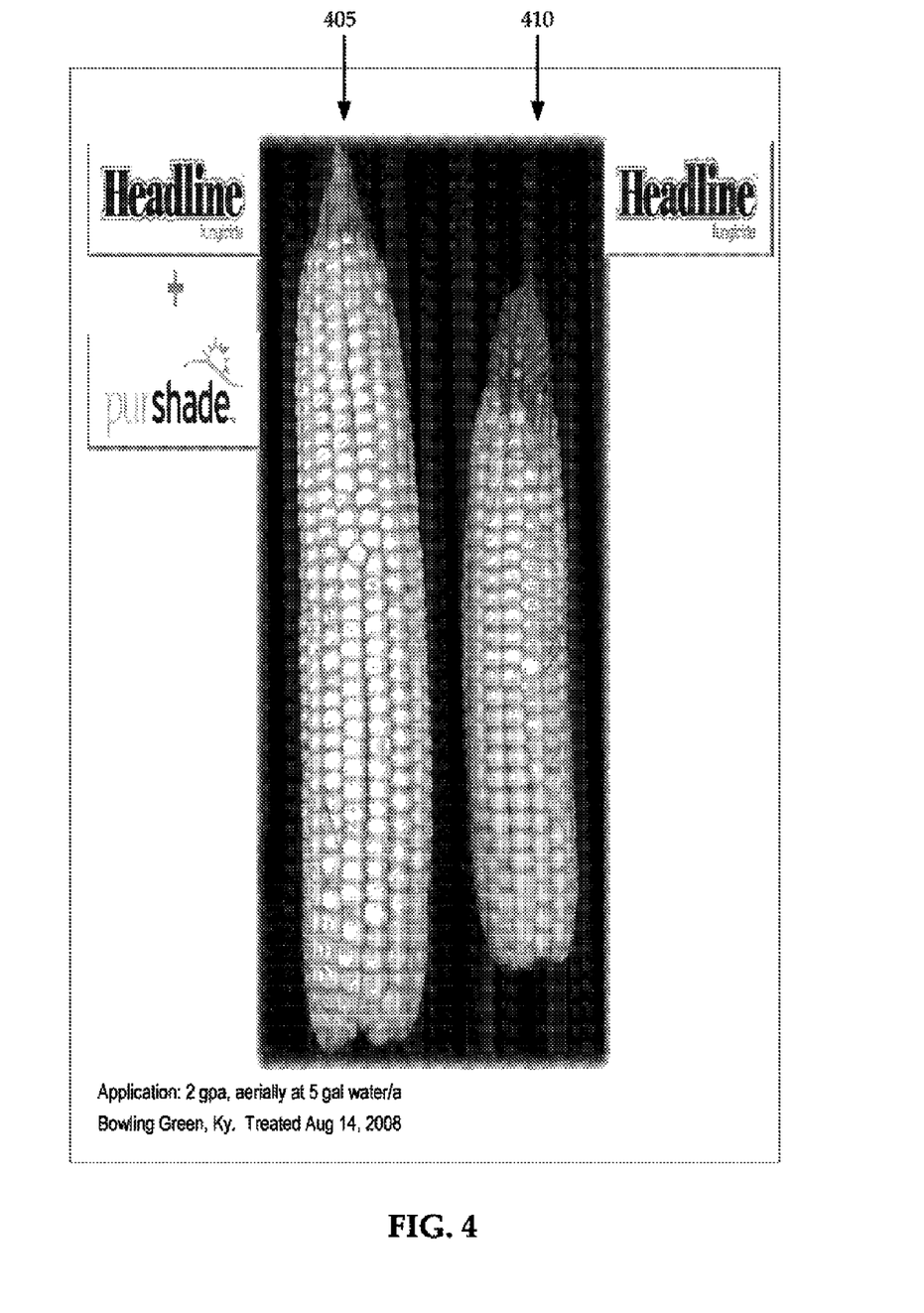

FIGS. 3-4 are photographs showing exemplary increased crop yield results in connection with Example One.

Fungal infection occurs in dead and senescing flower parts and invades through the stamens into the flower receptacle. A fungus can also invade necrotic areas of plant tissues. An outbreak of a fungus such as *botrytis* may be influenced by a complex set of factors. Climatic conditions such as high humidity, dew and intermittent rain during late season may influence an outbreak. Damage to plant tissues (e.g., by wind, birds, and/or insects) act as a stress factor which may offer a pathway for the fungus to enter the plant tissues. In the event of wounding, a combination of fresh wounds and free water promotes a fungal infection.

It has been found that applying a particle film that provides solar protection may also reduce the activity of plant pathogens. This suggests with applications of a particle film, a grower may apply less of a pesticide (fungicide) and still achieve acceptable control of plant pathogens.

EXAMPLE ONE

Referring now to FIG. 3, in Example One, corn was treated with a fungicide (Headline®) 305, or corn was treated with a combination of an agricultural sunscreen formulation (Purshade™) and a fungicide (Headline®) 310. Headline is a registered trademark of BASF. Specifically, the corn was treated on Aug. 14, 2008 in Bowling Green, Ky.

Referring now to FIG. 4, corn cobs 405 and 410 are shown. Corn cob 405 was treated with the combination of the agricultural sunscreen formulation (Purshade™) and the fungicide (Headline®). Corn cob 410 was treated with a fungicide (Headline®). The combination of the agricultural sunscreen formulation and the second agricultural chemical (fungicide) produced superior results.

Figure 5:
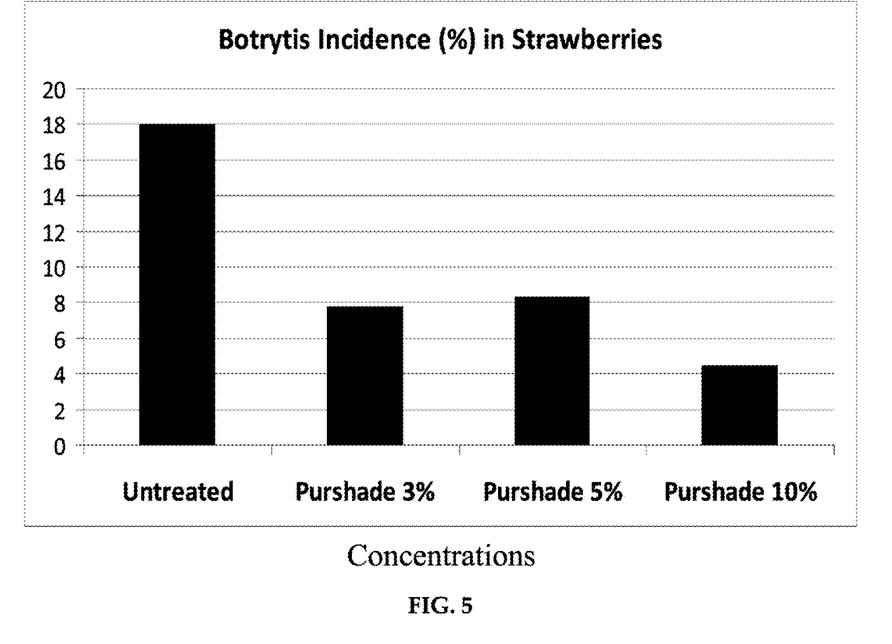
FIG. 5 is a chart showing exemplary increased crop yield results in connection with Example Two.

FIG. 5 is a chart showing exemplary increased crop yield results in connection with Example Two.

EXAMPLE TWO

Referring now to FIG. 5, strawberry plants were treated with varying concentrations of an agricultural sunscreen formulation (Purshade™). Specifically, the treatment concentrations were 3% Purshade™, 5% Purshade™, and 10% Purshade™. Some of the strawberry plants were not treated with the agricultural sunscreen formulation ("untreated"). The incidence (percentage) of *botrytis* fungal infection was calculated based on the various treatment groups. All groups treated with the agricultural sunscreen formulation produced superior (i.e. a lower incidence of *botrytis* infection) results over the untreated group.

Accordingly, collected data shows an agricultural sunscreen formulation alone reduces the incidence of *botrytis*. Synergies of an agricultural sunscreen formulation combined with an existing fungicide may result in broad spectrum fungal treatment and improved plant growth, including crop yield.

While various embodiments have been described herein, it should be understood that they have been presented by way of example only, and not limitation. Thus, the breadth and scope of a preferred embodiment should not be limited by any of the above-described exemplary embodiments.

The invention claimed is:

1. A method for controlling corn plant tissue stress, wherein the corn plant tissue is at least partially coating the corn plant tissue with a composition comprising an agricultural sunscreen formulation and a fungicide, the plant tissue stress caused at least in part by a fungus, and the agricultural sunscreen formulation comprising on a weight to weight basis about 40% to 80% calcium carbonate, about 1% to 5% of either sodium bicarbonate or potassium bicarbonate, and about 15% to 59% water.

2. The method of claim 1, wherein the fungus is *botrytis*.

3. A method for controlling corn plant tissue stress, wherein the corn plant tissue is at least partially coating the corn plant tissue with a composition comprising an agricultural sunscreen formulation and a fungicide, the plant tissue stress caused at least in part by a fungus, and the agricultural sunscreen formulation comprising on a weight to weight basis about 40% to 80% calcium carbonate, about 0% to 8% glycerin, about 0.1% to 0.5% of either sodium bicarbonate or potassium bicarbonate, and about 11.5% to 59.9% water.

4. A method for controlling strawberry plant tissue stress, wherein the strawberry plant tissue is at least partially coating the strawberry plant tissue with a composition comprising an agricultural sunscreen formulation, the plant tissue stress caused at least in part by a fungus, and the agricultural sunscreen formulation comprising on a weight to weight basis about 40% to 80% calcium carbonate, about 1% to 5% of either sodium bicarbonate or potassium bicarbonate, and about 15% to 59% water.

5. The method of claim 3, wherein the fungus is *botrytis*.

6. The method of claim 4, wherein the fungus is *botrytis*.

7. The method of claim 2, the method further comprising monitoring the plant tissue.

8. The method of claim 7, wherein the monitoring is performed by a plant tissue sensor.

9. The method of claim 8, wherein the plant tissue sensor provides a sap-flow measurement.

10. The method of claim 1, the composition further comprising a herbicide.

11. The method of claim 1, the composition further comprising a pesticide.

12. The method of claim 1, wherein the fungicide includes pyraclostrobin.

13. The method of claim 1, wherein the fungicide includes chlorothalonil.

14. The method of claim 2, wherein the *botrytis* is located in a necrotic plant tissue.

15. The method of claim 3, the method further comprising monitoring the plant tissue.

16. The method of claim 15, wherein the monitoring is performed by a plant tissue sensor.

17. The method of claim 16, wherein the plant tissue sensor provides a sap-flow measurement.

18. The method of claim 4, the method further comprising monitoring the plant tissue.

19. The method of claim 18, wherein the monitoring is performed by a plant tissue sensor.

20. The method of claim 19, wherein the plant tissue sensor provides a sap-flow measurement.

\* \* \* \* \*